United States Patent [19] [11] 4,209,467
Kojima et al. [45] Jun. 24, 1980

[54] HYDROFORMYLATION PROCESS

[75] Inventors: Hidetaka Kojima; Shingo Oda; Takushi Yokoyama; Yasukazu Murakami, all of Saitama, Japan

[73] Assignee: Daicel Ltd., Osaka, Japan

[21] Appl. No.: 269

[22] Filed: Jan. 2, 1979

[30] Foreign Application Priority Data

Jan. 17, 1978 [JP] Japan ................................. 53-3459
Feb. 13, 1978 [JP] Japan ................................ 53-14051

[51] Int. Cl.$^2$ ............................................. C07C 45/10
[52] U.S. Cl. ................................. 260/340.7; 568/909;
252/431 N; 568/456; 568/444; 560/233;
560/175; 568/429
[58] Field of Search ................. 260/604 HF; 568/909;
252/431 N

[56] References Cited

U.S. PATENT DOCUMENTS

| 3,560,572 | 2/1971 | Deffner et al. | 260/604 HF |
| 3,647,842 | 3/1972 | Wilkes | 260/604 HF |
| 3,647,845 | 3/1972 | Wilkes | 260/604 HF |
| 3,935,228 | 1/1976 | Keblys | 260/604 HF |
| 3,996,164 | 12/1976 | Matsuda | 260/604 HF |
| 4,096,188 | 6/1978 | Wilkes | 260/604 HF |

FOREIGN PATENT DOCUMENTS

| 1928101 | of 1969 | Fed. Rep. of Germany | 260/604 HF |
| 39-13059 | of 1964 | Japan | 260/604 HF |
| 50-45798 | of 1975 | Japan | 260/604 HF |
| 50-46589 | of 1975 | Japan | 260/604 HF |
| 50-62924 | of 1975 | Japan | 260/604 HF |
| 51-52389 | of 1976 | Japan | 260/604 HF |

OTHER PUBLICATIONS

5016 Japan, 1975, equiv. of U.S. Pat. No. 3,647,845.
507991, Japan, 1974, equiv. of U.S. Pat. No. 3,996,164.
5062925, Japan, 1975, equiv. of U.S. Pat. No. 2,447,069.
Chini, "Chim. et Ind." vol. 42, pp. 133-140.

Primary Examiner—Werren B. Lone
Attorney, Agent, or Firm—Blanchard, Flynn, Thiel, Boutell & Tanis

[57] ABSTRACT

A hydroformylation process in which the catalyst is the reaction product of a cobalt carbonyl compound with a nitrogen-containing heterocyclic compound having an enolic hydroxyl group on the carbon atom adjacent to the ring-forming nitrogen atom or the catalyst is the reaction product of a $\beta$-dioxo cobalt compound and a nitrogen-containing base having a double bonded carbon atom at the $\alpha$-position, with carbon monoxide and hydrogen.

16 Claims, No Drawings

HYDROFORMYLATION PROCESS

The present invention relates to a hydroformylation process using a novel cobalt catalyst.

The process in which a compound having an ethylenically unsaturated bond, such as ethylene or propylene, is reacted with carbon monoxide and hydrogen, in the presence of a catalyst, to effect hydroformylation and thereby obtain a corresponding aldehyde and, if desired, the resulting aldehyde is then further hydrogenated to obtain an alcohol, is well-known as the hydroformylation process or oxo process. As the catalyst for this reaction, there are frequently used carbonyl compounds of cobalt and rhodium.

An important cobalt carbonyl compound that is used as the catalyst for this hydroformylation process is dicobalt octacarbonyl, $Co_2(CO)_8$. Since this compound is readily decomposed if it is heated under a low partial pressure of carbon monoxide, various difficulties are encountered when the cobalt compound used for the reaction is separated from the reaction product and is employed for the reaction repeatedly. More specifically, according to a conventional recovery method, the cobalt catalyst is converted to metallic cobalt or an inert compound such as a cobalt salt, and therefore, in order to convert it to the active catalyst state again, a treatment under high pressure conditions is critically required. Further, when the carbon monoxide partial pressure is low, the problem of precipitation of metallic cobalt in the reaction system is caused to occur.

As means for stabilizing such cobalt carbonyl compound, there is known a process in which a complex compound is formed from the cobalt carbonyl compound and a ligand having an azoxy group (see U.S. Pat. No. 3,647,845). Azoxy ligands used in this known process are defined on Page 2 of that publication. They are compounds having nitrogen and oxygen atoms bonded through a chain of 2 or 3 carbon atoms so as to form a 5-membered or 6-membered heterocyclic ring with cobalt, namely, 1,4- and 1,5-azoxy compounds. According to this process, precipitation of metallic cobalt is prevented, but because the catalyst is dissolved in the reaction mixture, it is very difficult to separate the active compound directly from the reaction mixture and use it as the catalyst again. From experiments, we have confirmed that when 8-hydroxyquinoline, an example of these azoxy compounds, is employed, the reaction rate is reduced and good results cannot be obtained.

Matsuda proposed catalysts which can be recovered from liquid reaction mixtures by liquid-liquid phase separation and can be used for the reaction repeatedly (see U.S. Pat. No. 3,996,164 and Japanese Patent Application Laid-Open Specification No. 45798/75 and No. 46589/75). The catalysts proposed by Matsuda are complexes of cobalt carbonyls with carbonylation products or hydroesterification products of pyridine substituted with a specific unsaturated group (vinyl pyridine or dipyridyl ethylene). According to the predicted structures of these complexes as disclosed in these laid-open specifications, a chain of at least 3 or 4 carbon atoms is interposed between the nitrogen and oxygen atoms which are considered to participate in the formation of a cobalt complex. It is deemed that such catalyst is excellent in its separability from the liquid reaction mixture and it has a stability sufficient to withstand repeated use. However, for preparation of this catalyst, it is necessary to perform carbonylation or hydroesterification in the presence of high pressure carbon monoxide (plus hydrogen). A prepared catalyst has a considerable activity under a relatively low pressure of carbon monoxide of about 20 atmospheres, but for the preparation of the catalyst, per se, a high carbon monoxide pressure, such as more than 100 atmospheres, is necessary.

Rhodium is a metal which is not easily available. Therefore, improvements of the cobalt-type catalyst are important. One improvement of the cobalt-type catalyst is directed to the use of a nitrogen-containing base. The first example of this is disclosed in Japanese Pat. Publication No. 13059/64. In this publication, it is briefly described that prior to or simultaneously with the oxo reaction, a catalyst is prepared by reduction of a cobalt salt, but the process for the preparation of catalysts specifically disclosed in the Examples of this publication uses dicobalt octacarbonyl as the starting compound. For synthesis of dicobalt octacarbonyl from a customary cobalt salt, severe conditions such as a pressure of about 200 atmospheres and a temperature of about 200° C. are necessary. Therefore, in order to practice the process disclosed in this publication by using a cobalt salt as the starting compound, it is deemed necessary to employ such severe conditions.

In the field of the hydroesterification reaction, there has been developed a technique in which a common cobalt compound having no carbon monoxide ligand is used and carbonylation can be performed under a relatively low pressure (see Japanese Patent Application Laid-Open Specification No. 62925/75 and DOS No. 2 447 069). According to the teachings of these laid-open specifications, for example, $\gamma$-picoline is used in an amount of 10 moles per mole of cobalt octylate. Also in the field of the oxo reaction, a low pressure catalyst synthesis process has been developed from the above-mentioned technique. According to this process, a cobalt compound is reacted with carbon monoxide in the presence of a pyridine base in an amount exceeding the equimolar amount to form a cobalt carbonyl complex (see Japanese Patent Application Laid-Open Specification No. 52389/76). This laid-open specification describes Examples in which a cobalt carbonyl complex is synthesized under a relatively low pressure of 30 to 40 atmospheres. In these Examples, however, in addition to cobalt oxide, 5% of dicobalt octacarbonyl is used as the starting cobalt compound. If dicobalt octacarbonyl is used even in such a small amount as 5%, the industrial advantages of the low pressure synthesis are rather diminished. In other Examples, the amount of dicobalt octacarbonyl is reduced or dicobalt octacarbonyl is not used at all. In these Examples, however, a high pressure such as 150 atmospheres is employed for the synthesis.

If a catalyst reactive for the oxo reaction can be synthesized only from a customary cobalt compound having no carbon monoxide ligand, under a relatively low carbon monoxide partial pressure of up to several scores of atmospheres, it will be possible to prepare the catalyst in the same process as the low pressure oxo reaction without providing special high pressure equipment. Therefore, development of such a catalyst synthesis process has been eagerly desired in the art. This problem, however, has not been completely solved by any of the foregoing prior art techniques.

According to a prior art publication (P. Chini; Chim. et Ind., 42, 133–137 and 137–142, 1960), it is taught that when cobalt 2-ethylhexanoate or cobalt acetylacetonato is reacted, in the presence of dicobalt octacarbonyl, with carbon monoxide under a pressure of 30 to 130 atmospheres and hydrogen under a pressure of 40 to 200 atmospheres, at a temperature of 30° C., dicobalt octacarbonyl is formed in a yield of 80 to 90%. This process involves the same difficulties as are involved in the above-mentioned process of Japanese Patent Application Laid-Open Specification No. 52389/76. Namely, dicobalt octacarbonyl must be made present in the reaction system, and a sufficient reduction of the pressure cannot be attained.

According to the disclosure of German Patent Application Laid-Open Specification No. 1928101, a catalyst obtained by reacting cobalt acetylacetonato with ethoxydiethyl aluminum, in the presence of carbon monoxide under atmospheric pressure, can be used for the oxo reaction of cyclohexene. According to this process, however, a special reducing agent must be used, and this process is not a process based on hydrogen reduction.

Based on the foregoing prior art techniques in the hydroformylation process using a cobalt carbonyl compound as the catalyst, we have performed research with a view to developing a novel hydroformylation process in which the catalyst in the form of an active compound is excellent in its separability from the reaction mixture and in its stability, and a high pressure, such as above 100 atmospheres, need not be employed throughout the process, including the catalyst-preparation step. As a result, we have now completed the present invention.

More specifically, in accordance with the present invention, there is provided a hydroformylation process comprising reacting an ethylenically unsaturated compound with carbon monoxide and hydrogen, in the presence of a catalyst, said process being characterized by the features that the reaction is carried out in the presence of a catalyst formed by reaction between a cobalt carbonyl compound and a nitrogen-containing heterocyclic compound having an enolic hydroxyl group on the carbon atom adjacent to the ring-forming nitrogen atom (which compound is hereinafter referred to as "nitrogen-containing heterocyclic enolic compound").

In the present invention, the catalyst is formed by reaction between a cobalt carbonyl compound and a specific nitrogen-containing heterocyclic enolic compound, for example, 2-hydroxypyridine. There is a relation of tautomerism between 2-hydroxypyridine and 2-pyridone, and by the name of one compound, both the keto and enol compounds are included, as in ordinary tautomeric isomers. The same holds true with respect to the nitrogen-containing heterocyclic enolic compounds of the present invention described hereinafter, i.e., even if the name of a keto compound is used, a compound that can be converted to an enol compound is included in and is regarded as the enolic compound.

As the nitrogen-containing heterocyclic ring nucleus that can be used in the nitrogen-containing heterocyclic enolic compounds, according to the present invention, there can be mentioned, for example, a pyridine ring, a quinoline ring, an isoquinoline ring, a pyrimidine ring, a pyrazine ring, a quinoxaline ring, a pyrrole ring, a tetrahydropyridine ring, an oxazole ring and a dihydroxazine ring. However, a nitrogen-containing heterocyclic ring also containing a sulfur atom in the ring, such as a thiazole ring, is not preferred because it has adverse effects on the reaction. In these heterocyclic rings, at least 1 double bond should be present so as to make an enolic hydroxyl group present on the ring. These heterocyclic rings can have substituents, in addition to the enolic hydroxyl group on the carbon atom adjacent to the ring-forming nitrogen atom. As the substituents, there can be mentioned, for example, linear, alicyclic and aromatic hydrocarbon groups such as methyl, ethyl, allyl, 2-ethylhexyl, cyclohexyl, benzyl and phenyl groups, halogen atoms such as chlorine and bromine, halogen-containing groups such as a chloromethyl group, nitrogen-containing groups such as amino and cyano groups, oxygen-containing groups such as hydroxyethyl, methoxy, ethoxycarbonyl and carboxyl groups, and additional hydroxyl groups.

As typical examples of the nitrogen-containing heterocyclic enolic compound that can be used in the present invention, there can be mentioned, for example, in addition to the above-mentioned 2-hydroxypyridine, 2-hydroxy-5-methylpyridine (5-methyl-2-pyridone), 2-hydroxy-6-chloropyridine, 2-hydroxy-5-cyanopyridine, methyl 2-hydroxyisonicotinate, 2,6-dihydroxypyridine, 2-hydroxyquinoline, 1-hydroxyisoquinoline, 2,3-dihydroxyquinoxaline, 2-hydroxy-3,4,5,6-tetrahydropyridine (δ-valerolactam) and ε-caprolactam.

When the nitrogen-containing heterocyclic enolic compound is reacted with a cobalt carbonyl compound, such as dicobalt octacarbonyl or hydrocobalt tetracarbonyl, there is formed a catalyst, which is considered to be a complex compound of the two starting compounds. A special high pressure condition is not necessary for this catalyst-forming reaction. Namely, the reaction can be sufficiently carried out under a carbon monoxide partial pressure of 5 to 30 atmospheres at 50° to 60° C. or a higher temperature.

In the process of the present invention, the amount of the nitrogen-containing heterocyclic enolic compound can be equivalent to the amount of the cobalt atom, but even if the amount of the nitrogen-containing heterocyclic enolic compound is less than the equivalent amount, to our great surprise, the reaction rate is not reduced. In some cases, the reaction rate is highest if the amount of the nitrogen-containing heterocyclic enolic compound is about ½ equivalent to the amount of the cobalt atom. In general, the nitrogen-containing heterocyclic enolic compound is used in an amount of 0.25 to 2 equivalents to the amount of the cobalt atom.

For example, when dicobalt octacarbonyl in an amount of 1/50 mole per mole of a starting olefin and 2-hydroxypyridine in an amount of 2 moles per mole of dicobalt octacarbonyl, namely, in an equivalent amount to the amount of the cobalt atom, are charged in a reaction vessel together with the starting olefin and the mixture is heated while introducing carbon monoxide under a partial pressure of about 20 atmospheres and introducing hydrogen under a partial pressure of about 20 atmospheres, a catalyst is formed in the reaction mixture and the hydroformylation reaction is initiated. In this case, the temperature can be elevated at one time to a level suitable for the hydroformylation reaction, i.e., about 120° C., but better results are ordinarily obtained when the temperature is first elevated to about 60° C. to form the catalyst and then, the temperature is further elevated to a level suitable for the hydroformylation reaction.

In the present invention, the amount used of the nitrogen-containing heterocyclic enolic compound is relatively small as pointed out above. A pressure much higher than the pressure necessary for the hydroformylation reaction need not be employed for formation of the catalyst. In this point, the process of the present invention is advantageous over the prior art process developed by Matsuda in which a large amount of a pyridine compound is used (3.2 to 15 moles per mole of cobalt atom in the Examples), a catalyst is first formed by hydroformylation or hydroesterification of the ethylenically unsaturated structure of the pyridine compound, in the absence of the olefin, under a high pressure of at least 100 Kg/cm$^2$ and the intended hydroformylation or hydroesterification is then carried out under a lower pressure by using the thus-prepared catalyst. Of course, in the process of the present invention, it is possible to use a catalyst formed separately by heating the nitrogen-containing heterocyclic enolic compound and the cobalt carbonyl compound, without charging an olefin as the starting compound for hydroformylation. In this case, in order to prevent decomposition of the cobalt carbonyl compound, heating is carried out under pressurization with carbon monoxide, but good results are obtained even if the degree of pressurization is similar to that adopted for forming the catalyst in the hydroformylation reaction system. In this case, also, a particularly high pressure need not be adopted.

The term "cobalt carbonyl compound" used herein means a compound containing a cobalt atom and a carbon monoxide ligand. For example, dicobalt octacarbonyl and hydrocobalt tetracarbonyl are preferably employed.

Severe conditions, for example, a pressure of about 200 atmospheres and a temperature of about 200° C., are necessary for synthesizing dicobalt octacarbonyl, a typical example of the cobalt carbonyl compound, from a customary cobalt salt having no carbon monoxide ligand, but since dicobalt octacarbonyl is commercially available, if a commercially available product is employed, the process of the present invention can be carried out without providing any special high pressure equipment. However, the process of the present invention can be conveniently carried out even if a commercial product of dicobalt octacarbonyl is not used. Namely, the steps of preparing a cobalt carbonyl compound from a β-dioxo cobalt compound according to procedures described below and performing the hydroformylation reaction by using the thus-prepared cobalt carbonyl compound as the catalyst can be conducted consistently in one unitary process. In this case, a high pressure exceeding 100 atmospheres is not necessary at all and the process can be carried out very advantageously.

When the cobalt carbonyl compound and nitrogen-containing heterocyclic enolic compound are thus heated, there is formed a catalyst which is considered to be a complex of the two compounds. Formation of the catalyst and the hydroformylation reaction are ordinarily carried out in an organic solvent, but when the starting olefin reactant also acts as a solvent, it is not necessary to employ a special solvent in some cases. The solvent, when used, can be selected from known solvents for this reaction, for example, aromatic hydrocarbons such as benzene and toluene, aliphatic hydrocarbons such as hexane and heptane and oxygen-containing compounds such as acetone, diethylketone, benzophenone, tetrahydrofuran, dioxane and ethyl acetate. However, the selection of solvents is very important for carrying out the process of the present invention effectively. When the capacity for dissolving the nitrogen-containing heterocyclic enolic compound or other reactant or the reaction product is low, even if it is heated with the cobalt carbonyl compound, the catalyst is not satisfactorily formed. On the other hand, if the capacity for dissolving the catalyst is too high, the catalyst cannot be separated or recovered satisfactorily. Accordingly, in view of the foregoing, a suitable solvent should be selected depending on the kind of the reactant. For example, when 2-hydroxypyridine is employed, benzene is a suitable solvent. But when 2-hydroxyquinoline or 2,3-dihydroxyquinoxaline is used, because such compounds are insoluble in benzene, a solvent having a higher dissolving capacity, for example, tetrahydrofuran, is used. However, if the dissolving capacity of the solvent used is too high, the catalyst is not separated even by cooling the reaction mixture after completion of the reaction. In this case, benzene is added to the reaction mixture to effect separation or a mixed solvent is used for the reaction.

The present invention will now be described by reference to an embodiment in which hydroformylation is carried out by using a catalyst formed from 2-hydroxypyridine and dicobalt octacarbonyl, in benzene as the solvent.

Ethylene, carbon monoxide and hydrogen are introduced under pressure into a vessel charged with the above-mentioned solvent and the starting materials of the catalyst. When the mixture is heated, the catalyst-forming reaction is initiated at about 70° C. If the hydroformylation reaction is then carried out at a temperature set at 100° to 120° C., gas is absorbed more promptly than in the case where 2-hydroxypyridine is not added, and the reaction is advanced effectively.

The reaction can be conducted under a much lower pressure than the pressure of 200 to 300 atmospheres employed in the conventional hydroformylation process using a cobalt catalyst. In the present invention, the reaction pressure is ordinarily 30 atmospheres or a little higher. It is believed that this is owing to the characteristic feature of the present invention that the catalyst is stable and active under a low carbon monoxide partial pressure. The reaction pressure can be reduced to about 10 atmospheres. It is possible to elevate the reaction pressure to a level exceeding 100 atmospheres, but adoption of such high reaction pressure is not necessary. When the reaction is carried out batchwise, because large quantities of carbon monoxide, hydrogen, ethylene and other starting materials are charged, a relatively high initial pressure is sometimes employed. In this case, even if the pressure is reduced by consumption of the starting materials, with progress of the reaction, the reaction is conveniently conducted without any trouble.

The reaction temperature is at least 70° C., preferably 90° to 150° C. Other reaction conditions, for example, the amount of the catalyst used, based on the olefin, can be the same as ordinary hydroformylation conditions known in the art.

When the reaction mixture is cooled after completion of the reaction and the liquid is taken out, since the majority of the catalyst is separated in the form of a precipitate, the catalyst can easily be recovered from the liquid. Since this catalyst is stable even under heating without pressurization with carbon monoxide, the catalyst can be completely recovered by removing the hydroformylation product from the liquid reaction product by distillation and separating the catalyst from the residual liquid. From the results of the elementary analysis and infrared absorption spectrum analysis of the separated catalyst, it is construed that the catalyst has a structure in which carbon monoxide and 2-hydroxypyridine coordinate with cobalt.

The present invention can be applied to hydroformylation of not only hydrocarbons such as ethylene, propylene, 1-hexene, 2-octene, 1-decene, 2-ethyl-1-octene, cyclohexene, butadiene and styrene, but also other various ethylenically unsaturated compounds such as allyl alcohol, allyl acetate, 1,1-diethoxy-propene-2 and methyl acrylate.

In the hydroformylation process of the present invention, using a catalyst formed by reaction between a cobalt carbonyl compound and a nitrogen-containing heterocyclic compound having an enolic hydroxyl group on the carbon atom adjacent to the ring-forming nitrogen atom, because the thermal stability of the catalyst is high, separation of the hydroformylation product can be performed by distillation in the presence of the catalyst. Accordingly, the process of the present invention is advantageous not only in the point that the catalyst can be recovered by phase separation in condition for use in the reaction repeatedly, but also in the ease of preparation of the catalyst and other catalyst preparation conditions such as the starting compounds and the reaction pressure. Moreover, the process of the present invention is excellent in the selectivity to the hydroformylation reaction and in the reaction speed.

Even if various nitrogen-containing heterocyclic compounds such as pyridine, pyrimidine, imidazole and phenanthroline are used in combination with dicobalt octacarbonyl, the selectivity to hydroformylation or the reaction speed is rather reduced or is scarcely increased. The same holds true with respect to 2-picoline, 2-vinylpyridine, 2-chloropyridine, 3-cyanopyridine, 2,4-lutidine, 2-methyl-5-ethylpyridine, 2-mercaptopyridine and picolinic acid. It was found that the reaction speed can be increased by the use of certain compounds, for example, 2-aminopyridine and isoquinoline, but no satisfactory results can be obtained with respect to the selectivity to the hydroformylation reaction and the separability of the catalyst. It has been confirmed that 8-hydroxyquinoline disclosed in Japanese Patent Publication No. 16/75 provides a solid complex which can be separated, but this catalyst is not advantageous because the reaction speed is very low. 2-Hydroxymethylpyridine 2-($\beta$-hydroxyethyl)pyridine, which are included in the category of the azoxy chelate ligand defined in this prior art, do not form catalysts that can be recovered by phase separation and the reaction speed is lower than the reaction speed attained when only dicobalt octacarbonyl is used as the catalyst. When 3-hydroxypyridine or 4-hydroxypyridine is employed, the reaction speed is slightly increased, but no separable catalyst is formed and the selectivity is inferior to some extent. From the foregoing description, it will readily be understood that it is very difficult to prepare catalysts comparable to or superior to the catalyst invented by Matsuda by using pyridine and analogous compounds, without adoption of a high pressure such as exceeding 100 atmospheres.

To our great surprise, however, it was found that when certain hydroxyl derivatives such as 2-hydroxypyridine and 2-hydroxyquinoline are used, catalysts which are excellent not only in the separability but also in the selectivity and the reaction speed, can be obtained without employing a high pressure. As a result of our investigations, it was found that in order to obtain such an excellent catalyst without employing a high pressure, it is critical that an enolic hydroxyl group is present on the carbon atom adjacent to the ring-forming nitrogen atom. In these compounds, since the oxygen atom is separated from the nitrogen atom only by one carbon atom, if it is intended to form a cobalt-containing chelate ring, a 4-membered ring is inevitably formed and from general chemical knowledge, it was considered that the use of such compound would be disadvantageous. To our great surprise, however, it was found that only when such compound is used, can there be obtained a catalyst valuable for attaining the objects of the present invention. Based on this finding, the present invention has been completed.

We conducted further research with a view to developing a process in which a catalyst effective in the oxo reaction is prepared by reducing a common cobalt compound with hydrogen under a relatively low carbon monoxide partial pressure, without the necessity of charging a cobalt carbonyl compound to the reaction system at all. As a result, we have now completed the following process.

More specifically, in accordance with another aspect of the present invention, there is provided a process for the preparation of catalysts for the oxo reaction, which comprises reacting a $\beta$-dioxo cobalt compound and a nitrogen-containing base having a double bonded carbon atom at the $\alpha$-position, with carbon monoxide and hydrogen.

As the $\beta$-dioxo cobalt compound that can be used in the present invention, there can be mentioned, for example, compounds formed from cobalt and $\beta$-diketones such as acetylacetone, 3-methyl-2,4-pentanedione, propionylacetone, benzoylacetone and benzoylacetophenone, $\beta$-keto acid esters such as methyl acetoacetate, ethyl acetoacetate, ethyleneglycol diacetoacetate, ethyl propionylacetate, methyl butyrylacetate and $\alpha$-acetyl-$\gamma$-butyrolactone, malonic acid esters such as diethyl malonate and diethyl methylmalonate, or compounds ($\beta$-dioxo compounds) having a structure

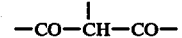

in the molecule, such as dehydroacetic acid. As specific examples, there can be mentioned bisacetylacetonato-cobalt, bispropionylacetonato-cobalt, bis(methylacetoacetato)-cobalt and bis(diethylmalonato)-cobalt. Among these compounds, bisacetylacetonato-cobalt is readily available and is soluble in an organic solvent. Accordingly, this compound can easily be handled. Moreover, the resulting catalyst is a liquid that can easily be separated. Therefore, this compound is especially preferably used in the present invention.

In the present invention, in forming an oxo reaction catalyst having a carbon monoxide ligand by reacting the above-mentioned cobalt compound having no carbon monoxide ligand with carbon monoxide and hydrogen, the reaction is carried out in the presence of a nitrogen-containing base having a double bonded carbon atom at the $\alpha$-position. The term "$\alpha$-position" herein means a position adjacent to the nitrogen atom. The term "nitrogen-containing base having a double bonded carbon atom at the $\alpha$-position" means a nitrogen-containing base in which the carbon atom present at the above-mentioned $\alpha$-position is bonded to another atom through a double bond, for example, C=C, C=N or C=O bond. This double bond can be a part of a ring having a conjugated double bond. More specifically, there can be used nitrogen-containing heterocyclic compounds having an $\alpha$-double bond, such as pyridine bases and quinoline bases, aromatic amines such as aniline, and amides inclusive of lactams. These compounds are different from other nitrogen-containing bases such as alkylamines and piperidine in the point that the basicity is very low. When the basicity is expressed by the pKa value (at 25° C.) of the conjugated acid of the base, pyridine, α-picoline and aniline, which are used in the present invention, have pKa values of 5.2, 6.2 and 4.6, respectively. The pKa values of triethylamine and piperidine, on the other hand, are 10.9 and 11.1, respectively. Thus, the base that can be used in the present invention is a weak base having a pKa value lower than 7. Among these bases, nitrogen-containing heterocyclic compounds having a conjugated double bond, such as pyridine and quinoline, and compounds having an isoquinoline nucleus are especially preferred. The nuclei of these compounds can be substituted with substituents, for example, linear, alicyclic and aromatic hydrocarbon groups such as methyl, ethyl, propyl, allyl, 2-ethylhexyl, cyclohexyl, benzyl and phenyl groups, halogen atoms such as chlorine and bromine, halogen-containing groups such as a chloromethyl group, nitrogen-containing groups such as amino and cyano groups, and oxygen-containing groups such as hydroxyl, methoxy, ethoxycarbonyl and hydroxyethyl groups.

Specific examples of the nitrogen-containing heterocyclic compound having a double bonded carbon atom at the α-position that can be used in the present invention include 2-pyridone, 5-methyl-2-pyridone, 6-chloro-2-pyridone, 5-cyano-2-pyridone, methyl 2-hydroxyisonicotinate, 2,6-dihydroxypyridine, 2-hydroxyquinoline, 1-hydroxyisoquinoline, 2,3-dihydroxyquinoxaline, 3-pyridone, 4-pyridone, 8-hydroxyquinoline, 2-pyridyl methanol, 2-(2-pyridyl) ethanol, 2-aminopyridine, picolinic acid, 3-cyanopyridine, 2-chloropyridine, 2-vinyl-pyridine, 2,4-lutidine, 3,4-lutidine, 2,6-lutidine, 3,5-lutidine, 2,4,6-collidine, 2-methyl-5-ethylpyridine, 2-propylpyridine, 2-ethylpyridine, α-picoline, β-picoline, γ-picoline and pyridine.

When the above-mentioned β-dioxo cobalt compound and nitrogen-containing base having a double bonded carbon atom at the α-position are combined and they are reacted with carbon monoxide and hydrogen, an oxo reaction catalyst can be formed even without charging any cobalt carbonyl compound into the reaction system at all. Further, a particularly high pressure, such as above 100 Kg/cm², need not be employed. If each of the partial pressures of carbon monoxide and hydrogen is about 20 Kg/cm², which is equal to the pressure adopted for the oxo reaction using the catalyst prepared according to the present invention, satisfactory results can be obtained.

In the present invention, a nitrogen-containing base having a double bonded carbon atom at the α-position, such as 2-pyridone (2-hydroxypyridine) is used, as mentioned above. In the present invention, it is critical that the cobalt compound that is combined and reacted with the nitrogen-containing base should be a β-dioxo cobalt compound.

As the common cobalt compounds, there can be mentioned cobalt oxide, cobalt hydroxide, basic cobalt carbonate, cobalt acetate and cobalt octylate. The invention disclosed in Japanese Patent Application Laid-Open Specification No. 52389/76 is characterized in that such common cobalt compound is used as the main starting material in combination with a pyridine base in an amount exceeding the equimolar amount. However, if only such a cobalt compound having no carbon monoxide ligand is used, the catalytic activity is low, and therefore, dicobalt octacarbonyl must be used as a subsidiary starting material together with such cobalt compound in preparing a catalyst or a very high pressure must be used so as to increase the catalytic activity.

This disadvantage of the above prior art process was confirmed by the experiments made by us. More specifically, it was found that when such common cobalt compound and 2-pyridone are charged and the oxo reaction is attempted under a low pressure, gas absorption is not caused and no catalyst is formed under CO and $H_2$ partial pressures of about 20 atmospheres. However, to our great surprise, it was found that when bisacetylacetonato-cobalt, which does not have a carbon monoxide ligand but rather has a β-dioxo compound ligand, is used in combination with 2-pyridone, the reaction is initiated at about 150° C. even without adopting special conditions for the preparation of the catalyst, and formation of a cobalt carbonyl compound, formation of the catalyst by reaction with 2-pyridone and the oxo reaction promoted by this catalyst are advanced in one unitary process. The bisacetylacetonato-cobalt can be either an anhydride or a dihydrate. Even if cobalt hydroxide and acetylacetone are charged, instead of bisacetylacetonato-cobalt, and they are reacted to form a β-dioxo cobalt compound, the reaction is tentatively advanced, but the obtained results are inferior to the results obtained when bisacetylacetonato-cobalt prepared in advance is employed.

Other β-dioxo compounds mentioned hereinbefore (β-diketones, βketo acid esters, malonic acid esters and dehydroacetic acid) can be used as the β-dioxo compound component, and cobalt compounds prepared by combining these β-dioxo compounds with cobalt can be effectively employed. Namely, an oxo reaction catalyst can be prepared by reacting such a β-dioxo cobalt compound and a nitrogen-containing base having a double bonded carbon atom at the α-position, with carbon monoxide and hydrogen, without using a special reducing agent such as an alkyl metal compound or a reducing catalyst such as platinum, under a relatively low carbon monoxide partial pressure.

Various compounds such as those exemplified above can be used as the nitrogen-containing base having a double bonded carbon atom at the α-position. A catalyst prepared by using a nitrogen-containing base having a carbonyl carbon atom as the double bonded carbon atom at the α-position is especially preferred because it is very stable even under a low carbon monoxide partial pressure and it has a good separability from the liquid reaction mixture and it is therefore conveniently recovered and used for repeating the oxo reaction. As the heterocyclic compound having a carbonyl carbon atom at the α-position, 2-pyridone is especially preferred. There is a relation of tautomerism between 2-pyridone and 2-hydroxypyridine, and by the name of one compound, both the keto and enol compounds are included, as in ordinary tautomeric isomers. The same holds true with respect to heterocyclic compounds having a carbonyl carbon atom at the α-position, which will be exemplified hereinafter, and even if the name of an enol type compound is used, a compound that can be converted to a keto type is included in and regarded as the keto-type compound.

As the heterocyclic compound having a carbonyl carbon atom at the α-position, that can be used in the present invention, there can be mentioned, for example, 2-pyridone, 5-methyl-2-pyridone, 6-chloro-2-pyridone, 5-cyano-2-pyridone, methyl 2-hydroxyisonicotinate, 2,6-dihydroxypyridine, 2-hydroxyquinoline, 2,3-dihydroxyquinoxaline, δ-valerolactam and ε-caprolactam.

A catalyst which can be recovered as an active cobalt carbonyl compound by liquid-liquid phase separation from the liquid reaction mixture and can be used repeatedly for the oxo reaction has already been proposed by Matsuda (see Japanese Patent Application Laid-Open Specifications No. 79991/74, No. 45798/75 and No. 46589/75). This known catalyst is a complex of a carbonylation product or hydroesterification product of vinylpyridine or divinylethylene with a cobalt carbonyl compound, and it is excellent in its separability from the liquid reaction mixture and it has a stability sufficient to resist repeated use. However, in order to prepare this catalyst, the use of dicobalt octacarbonyl is indispensable and carbonylation or hydroesterification must be carried out in the presence of high pressure carbon monoxide (plus hydrogen). Once the catalyst is prepared it has a considerable activity under a relatively low pressure of about 20 atmospheres, but a high pressure exceeding 100 atmospheres is necessary for preparing same. On the other hand, in the process of the present invention using, for example, bisacetylacetonato-cobalt and 2-pyridone, dicobalt octacarbonyl need not be used at all and a particularly high pressure need not be adopted for the preparation of a catalyst. There is known a technique according to which a cobalt compound is stabilized by a 1,4- or 1,5-azoxy compound having nitrogen and oxygen atoms bonded through a chain of 2 or 3 carbon atoms and precipitation of metallic cobalt is thus prevented (see Japanese Patent Publication No. 16/75). In the predicted structure of the above-mentioned catalyst proposed by Matsuda, nitrogen and oxygen atoms are bonded through a chain of at least 3 or at least 4 carbon atoms. The present invention using an α-carbonyl compound as the nitrogen-containing base having a double bonded carbon atom at the α-position is in agreement with these prior art techniques in the point that there is present a linkage of $N-C_n-O$. However, in the prior art techniques, n is at least 2, but in the present invention, n is 1. From general chemical principles, the case of n = 1 is very disadvantageous for formation of a cobalt chelate ring. Nevertheless, in the present invention, a catalyst that can easily be recovered is prepared under a low pressure even though this case was previously considered disadvantageous. This is quite a surprising finding.

The amount used of the nitrogen-containing base having a double bonded carbon atom at the α-position can be equivalent to the amount of the cobalt atom. To our great surprise it was found that even if the amount of the base is reduced below the equimolar amount, the reaction rate is not lowered and it sometimes happens that a maximum reaction speed can be attained when the amount of the base is about 0.5 equivalent to the amount of the cobalt atom. In general, the base is used in an amount of 0.25 to 2 equivalents to the amount of the cobalt atom. This amount partially overlaps the pyridine base/cobalt ratio disclosed in the above-mentioned Japanese Patent Application Laid-Open Specification No. 52389/76, but the amount of the base used in the present invention is rather on the smaller side.

When a β-dioxo cobalt compound and a nitrogen-containing base having a double bonded carbon atom at the α-position are heated with carbon monoxide and hydrogen and they are thus reacted, an excellent catalyst as mentioned above is formed. In this case, the formation of the catalyst and its function in the hydroformylation process are the same as in the case of the foregoing catalyst formed from a cobalt carbonyl compound and a nitrogen-containing heterocyclic compound of the enol type.

The present invention will now be described by reference to an embodiment in which hydroformylation of ethylene is carried out by using a catalyst formed from 2-pyridone and bisacetylacetonato-cobalt in the presence of benzene as a solvent.

Ethylene, carbon monoxide and hydrogen are fed under pressure into a vessel in which the above-mentioned solvent and catalyst-forming starting compounds are charged, and heating is carried out under a pressure of at least 20 atmospheres, preferably at least 30 atmospheres, the reaction is initiated at about 150° C., and the oxo reaction is then conducted at a temperature set at 100° to 120° C.

The reaction conditions in the hydroformylation using this type of catalyst is the same as in the case of the foregoing catalyst formed from a cobalt carbonyl compound and a nitrogen-containing heterocyclic compound of the enol type. After completion of the reaction, the liquid reaction mixture is cooled and taken out, and when propionaldehyde is removed by distillation, the catalyst is phase-separated in the form of a reddish brown oily substance. It is stated that the catalyst according to the invention of Matsuda is in the form of a dark red viscous liquid. The above catalyst of the present invention is not viscous, and it is excellent in its separability from the liquid reaction mixture and it has no adhesiveness to the vessel wall. This oily catalyst is well soluble in acetone, diethylketone and propanol and it is slightly soluble in ether and benzene, but it is insoluble in hexane and heptane. Accordingly, high-boiling-point impurities contained in the catalyst can easily be removed by washing with hexane.

From the results of the elementary analysis and infrared absorption spectrum analysis, it is judged that the catalyst has a basic structure in which carbon monoxide and 2-pyridone coordinate with cobalt as in case of the above-mentioned catalyst. It is construed that compounds formed by hydrogenation, hydroformylation and condensation of a part of acetylacetone are bonded to this basic structure and therefore, the crystalline catalyst is converted to an oily substance. When bis(methylacetoacetato)-cobalt is employed instead of bisacetylacetonato-cobalt, a small amount of skin-colored crystals is formed in addition to the liquid catalyst.

The catalyst, after being phase-separated from the reaction mixture formed by the first oxo reaction or catalyst-forming reaction using the β-dioxo compound and the nitrogen-containing base having a double bonded carbon atom at the α-position, can be used again and it possesses an activity sufficient for the reaction using a fresh ethylenically unsaturated compound. When bisacetylacetonato-cobalt and 2-pyridone are used, at the first hydroformylation reaction, the temperature is once elevated for initiation of the reaction, and it sometimes happens that the selectivity to the oxo reaction is low. However, the catalyst prepared in the same process as that of the reaction shows a high selectivity in the second or subsequent oxo reactions. In order to obtain, with assurance, a high selectivity even in the first oxo reaction, it is recommended to employ a method in which a preliminary synthesis of the catalyst is carried out in a reaction vessel in which an olefin is not charged and then, the olefin is charged into the reaction vessel and the first oxo reaction is carried out.

Also when a nitrogen-containing base in which the double bonded carbon atom at the α-position is not a carbonyl carbon atom, such as pyridine or 2-ethylpyridine, is used, instead of 2-pyridone, the β-dioxo cobalt compound having no carbon monoxide ligand is similarly reduced and carbonylated under low pressure oxo reaction conditions to form an oxo reaction catalyst, and if ethylene is charged in the reaction vessel, the oxo reaction is subsequently performed to form propionaldehyde. However, in this case, the catalyst is inferior to the catalyst prepared by using 2-pyridone with respect to its separability from the liquid reaction mixture after the reaction and its adaptability to repeated use.

The present invention can be applied to formation of catalysts for the oxo reaction of not only hydrocarbons such as ethylene, propylene, 1-hexene, 2-octene, 1-decene, 2-ethyl-1-octene, cyclohexene, butadiene and styrene, but also other various ethylenically unsaturated compounds such as allyl alcohol, allyl acetate, 1,1-diethoxypropene-2 and methyl acrylate.

According to the process of the present invention for preparing a catalyst by reacting a β-dioxo cobalt compound and a nitrogen-containing base having a double bonded carbon atom at the α-position, with carbon monoxide and hydrogen, even if only the above cobalt compound having no carbon monoxide ligand is used as the cobalt component, the intended excellent catalyst can be obtained under relatively low pressure oxo reaction conditions. Therefore, the process of the present invention is advantageous with respect to the starting material and the reaction equipment, and it is also excellent in the speed of the oxo reaction.

When the hydroformylation reaction is carried out by using one of the above-mentioned two types of catalysts, if the reaction mixture is cooled and the intended product is distilled under reduced pressure, the catalyst can be separated and recovered in the form of a precipitate or an oil.

The catalyst can be separated substantially completely by distillation of the majority of the product, such as propionaldehyde, in the case of either solid-liquid separation or liquid-liquid separation.

When polyethylene glycol (PEG) or dimethylformamide is added in an appropriate amount to the liquid reaction mixture, the catalyst can be completely separated from the liquid reaction mixture taken out without pressurization with carbon monoxide or hydrogen by liquid-liquid separation, even when the distillation treatment is not performed. For this separation method, for example, polyethylene glycol having an average molecular weight of 400 (PEG-400) is used. When polyethylene glycol having too large a molecular weight is employed, a solidification tendency is observed and the liquid-liquid phase separation becomes difficult. Accordingly, polyethylene glycol having a molecular weight of up to about 600 is used. The terminal OH group of the polyethylene glycol thus added to the reaction mixture is capable of reacting with the resulting aldehyde, and therefore, the yield of the aldehyde in the first reaction is relatively reduced and this tendency is prominent when polyethylene glycol having a low molecular weight, for example, triethylene glycol, is used. However, in this case, in the second and subsequent reactions wherein the polyethylene glycol is used repeatedly together with the catalyst, a high selectivity to the intended aldehyde can be obtained. Polyethylene glycol is ordinarily used in a volume of about 0.5 to 0.5 times the volume of the aromatic hydrocarbon solvent used. If polyethylene glycol is used in such amount, the separation operation can be facilitated. The volume of the polyethylene glycol can be increased up to about 1 times the volume of the solvent. However, when polyethylene glycol is used in such a large amount as to replace the majority of the solvent, the gas absorption speed is drastically reduced. Polyethylene glycol per se is soluble in benzene, but even if it is used in combination with benzene as the solvent, it has such a capacity that the resulting reaction mixture is separated into a benzene liquid phase containing the resulting aldehyde and a polyethylene glycol liquid phase containing the catalyst.

Separation of the liquid reaction mixture into two phases by polyethylene glycol can be accomplished, for example in case of the benzene solvent, by allowing the liquid reaction mixture taken out under no pressurization with carbon monoxide or hydrogen to stand still for about 5 hours. When such liquid reaction mixture is maintained at 50° to 60° C. for 15 to 30 minutes or if a linear or alicyclic hydrocarbon solvent, such as hexane, is further added, the liquid-liquid phase separation is accelerated and promoted. Therefore, such means can be adopted if needed.

When ethylbenzene is used as the solvent, the phase separation by polyethylene glycol can be accomplished more promptly than in case of benzene. When dimethylformamide is used instead of polyethylene glycol, the effect of phase separation of the reaction mixture into the catalyst phase and the product phase can similarly be attained.

The hydroformylation catalyst according to the present invention is much superior compared to the conventional catalysts with respect to the thermal stability, and therefore, it can easily be separated from the reaction mixture by distillation of the formed aldehyde without pressurization with carbon monoxide or hydrogen. Further, when polyethylene glycol or dimethylformamide is used in the above-mentioned manner, the catalyst can be effectively separated from the reaction mixture by the phase separation without heating and it can be used for the reaction repeatedly. When such a separation assistant is employed, even in the case of a catalyst formed by using dicobalt octacarbonyl, the catalyst is separated and recovered not in the form of a solid precipitate, but rather in the form of a liquid that can easily be handled. Moreover, the reactivity is enhanced by addition of polyethylene glycol or dimethylformamide.

The present invention will now be described in detail by reference to the following Examples that by no means limit the scope of the invention. In the Examples, the term "2-pyridone" also includes 2-hydroxypyridine. This is because the name given to the commercially available product is adopted. There is no other particular reason for use of this term.

EXAMPLE 1 (PREPARATION AND USE OF NOVEL CATALYST)

An autoclave having an inner capacity of 300 ml and equipped with a stirrer was charged with 2 millimoles of dicobalt octacarbonyl, 4 millimoles of 2-pyridone (2-hydroxypyridine) and 50 ml of benzene, and 98 millimoles of ethylene was filled in the autoclave together with carbon monoxide gas and hydrogen gas, each having a partial pressure of 22 Kg/cm$^2$, and the reaction was carried out at 120° C. for 15 minutes.

After the reaction, the autoclave was cooled, and when the residual gas was released and the liquid reaction mixture was taken out, the majority of the catalyst was precipitated in the form of skin-colored crystals. By distillation of the formed aldehyde, the amount of the crystals was increased, and the catalyst was separated from the benzene solution.

From the results of the gas chromatographic analysis of the product, it was found that the conversion of ethylene was 88%, the selectivity of the converted ethylene to propionaldehyde was 88% and trace amounts of n-propanol and ethane were formed. The gas absorption speed was 370 moles per mole of Co per hour.

EXAMPLE 2 (USE OF RECOVERED CATALYST)

The reaction was carried out under the same conditions as in Example 1 except that the catalyst recovered in Example 1 was used instead of dicobalt octacarbonyl and 2-pyridone. The conversion of ethylene was 91.0% and the selectivity of the converted ethylene to propionaldehyde was 85.0%. Trace amounts of n-propanol and ethane were formed. The ratio of recovery of the catalyst after the reaction was 95%.

EXAMPLE 3 (INFLUENCES OF AMOUNT ADDED OF 2-PYRIDONE)

The reaction was carried out under the same conditions as in Example 1 except that the amount added of 2-pyridone was changed as shown in Table 1. The results obtained are shown in Table 1.

TABLE 1

| Run No. | 2-Pyridone/ $Co_2(CO)_8$ Molar Ratio | Conversion (%) | Selectivity (%) to Propionaldehyde | Gas Absorption Speed (moles per mole of Co per hour) |
|---|---|---|---|---|
| 3A | 0.5 | 88.1 | 81.0 | 320 |
| 3B | 1.0 | 88.6 | 86.3 | 480 |
| 3C | 3.0 | 85.2 | 84.0 | 290 |

Even if 2-pyridone is used in an amount not larger than an amount equivalent to the cobalt atom (runs No. 3A and No. 3B), the reaction was advanced promptly, and the catalyst could be recovered by phase separation in the same manner as in Examples 1 and 2. For comparison, the reaction was carried out without using a nitrogen-containing heterocyclic compound such as 2-pyridone. In this comparative run, the gas absorption speed was 210 moles per mole of Co per hour (the conversion was 87% and the selectivity was 83%), and the catalyst was not phase-separated at all.

Comparative Examples 1 to 6 (Use of Compounds Having Non-Adjacent Hydroxyl Group)

The reaction was carried out in the same manner as in Example 1 except that instead of 2-pyridone, there were separately employed 3-pyridone, 4-pyridone, 8-hydroxyquinoline, 2-hydroxymethylpyridine, 2-($\beta$-hydroxyethyl)pyridine and 2-($\gamma$-hydroxypropyl)pyridine. The results shown in Table 2 were obtained. When 8-hydroxyquinoline was used, the catalyst was separated in the form of a solid, but the reaction rate was very low. In case of the other compounds, phase separation of the catalyst did not occur at all.

TABLE 2

| Run No. | Nitrogen-Containing Heterocyclic Compound | Conversion (%) | Selectivity (%) to Propionaldehyde | Gas Absorption Speed (moles per mole of Co per hour) | Reaction time (minutes) |
|---|---|---|---|---|---|
| 1 | 3-pyridone | 80.2 | 73.9 | 259 | 20 |
| 2 | 4-pyridone | 85.8 | 76.5 | 316 | 20 |
| 3 | 8-hydroxyquinoline | 91.3 | 78.0 | 39 | 80 |
| 4 | 2-(hydroxymethyl)-pyridine | 89.2 | 80.8 | 166 | 30 |
| 5 | 2-($\beta$-hydroxyethyl)-pyridine | 82.2 | 72.5 | 84 | 40 |
| 6 | 2-($\gamma$-hydroxypropyl)-pyridine | 82.8 | 71.0 | 60 | 70 |

EXAMPLE 4

The same autoclave as used in Example 1 was charged with 2 millimoles of dicobalt octacarbonyl, 4 millimoles of 2-pyridone of 50 ml of benzene, and 100 millimoles of propylene was filled in the autoclave, together with carbon monoxide gas of a pressure of 44 $Kg/cm^2$ and hydrogen gas of a pressure of 44 $Kg/cm^2$. The reaction was carried out at 80° C. for 5 hours. Conversion of propylene was 94.7% and the formed aldehyde comprised 75.4% of n-butyraldehyde and 24.6% of isobutyraldehyde. The catalyst was phase-separated, and it could easily be recovered and used repeatedly.

EXAMPLE 5

An autoclave was charged with 2 millimoles of dicobalt octacarbonyl, 4 millimoles of 2-hydroxyquinoline and 50 ml of tetrahydrofuran, and 98 millimoles of ethylene was filled in the autoclave, together with carbon monoxide gas of a pressure of 22 $Kg/cm^2$ and hydrogen gas of a pressure of 22 $Kg/cm^2$. The reaction was carried out at 120° C. for 15 minutes. The gas absorption speed was 295 moles per mole of Co per hour. The selectivity to propionaldehyde was 73.3%.

EXAMPLE 6

A micro-bomb having an inner capacity of 50 ml was charged with 0.4 millimoles of dicobalt octacarbonyl, 0.82 millimole of 2-pyridone, 10 ml of benzene and 28.71 millimoles of allyl acetate, and carbon monoxide gas under a pressure of 30 $Kg/cm^2$ and hydrogen gas under a pressure of 30 $Kg/cm^2$ were filled in the micro-bomb. The reaction was carried out at 90° C. for 3.5 hours. The conversion of allyl acetate was 100% and the selectivity to 4-acetoxybutyraldehyde was 63.5%. The gas absorption speed was 32 moles per mole of Co per hour, which was about 3 times as high as the gas absorption speed attained when 2-pyridone was not added.

EXAMPLE 7

The reaction was carried out in the same manner as in Example 6 except that 30.61 millimoles of 2-vinyl-4-methyl-1,3-dioxane was used instead of allyl acetate. The conversion of 2-vinyl-4-methyl-1,3-dioxane was 100%, and the selectivity to 2-(3'-propanal)-4-methyl-1,3-dioxane was 83% and the selectivity to 2-(2'-propanal)-4-methyl-1,3-dioxane was 11.4%, the total selectivity to the hydroformylation products being 92.3%. The gas absorption speed was 34 moles per mole of Co per hour, which was about 3 times as high as the gas absorption speed attained when 2-pyridone was not added.

EXAMPLE 8

The same autoclave as used in Example 1 was charged with 4 millimoles of bis(acetylacetonato)-cobalt, 4-millimoles of 2-pyridone and 50 ml of benzene, and 98 millimoles of ethylene was filled in the autoclave together with carbon monoxide of a pressure of 22 $Kg/cm^2$ and hydrogen of a pressure of 22 $Kg/cm^2$. When the autoclave was heated, the reaction was initiated at 148° C., and this temperature was maintained for 15 minutes. Then, the autoclave was cooled and the residual gas was released. From the results of the gas chromatography analysis of the product, it was found that the conversion of ethylene was 91.0%, and the selectivity of the converted ethylene to propionaldehyde was 66.7% and the selectivities of the converted ethylene to n-propanol and ethane were 5.7% and 3.9%, respectively. The gas absorption speed was 699 moles per mole of Co per hour. When the formed aldehyde was removed from the liquid mixture, the catalyst was separated in the form of a dark red oily substance.

EXAMPLE 9

A small amount of the liquid reaction mixture obtained in Example 8 was condensed and high-boiling-point products were separated by extraction with n-hexane. The residue was charged in the same autoclave as used in Example 1, and 50 ml of benzene was added thereto. Then, 98 millimoles of ethylene was filled in the autoclave together with carbon monoxide of a pressure of 22 $Kg/cm^2$ and hydrogen of a pressure of 22 $Kg/cm^2$. The reaction was carried out at 120° C. for 15 minutes. From the results of the analysis of the product, it was found that the conversion of ethylene was 86.2%, the selectivity of the converted ethylene to propionaldehyde was 92.3% and trace amounts of n-propanol and ethane were formed. The catalyst was recovered in the form of an oily substance and it could be used repeatedly for the reaction.

EXAMPLE 10

The reaction was carried out under the same conditions as in Example 8 except that bis(methylacetoacetato)-cobalt was used instead of bisacetylacetonato-cobalt. The reaction was initiated at 160° C., and this temperature was maintained for 15 minutes. The conversion of ethylene was 86.3%, and the selectivities of the converted ethylene to propionaldehyde, n-propanol and ethane were 55.0%, 15.8% and 2.3%, respectively. The gas absorption speed was 885 moles per mole of Co per hour. The majority of the catalyst was separated in the form of a liquid, but a small amount of the catalyst was separated in the form of a crystalline precipitate.

EXAMPLE 11

A product prepared in the reaction system from 4 millimoles of cobalt hydroxide and 8 millimoles of acetylacetone was used instead of 4 millimoles of the commercially available product of bisacetylacetonato-cobalt used in Example 8. The other starting materials were the same as those used in Example 8. The reaction was carried out at 200° C. for 2 hours. A small amount of propionaldehyde was obtained. When cobalt oxide was used instead of cobalt hydroxide, the reaction did not occur at all.

For comparison, cobalt octylate, cobalt acetate tetrahydrate or basic cobalt carbonate (4 millimoles as cobalt) was used instead of acetylacetone together with 4 millimoles of 2-pyridone. In the same manner as in Example 8, ethylene, carbon monoxide of a pressure of 22 $Kg/cm^2$ and hydrogen of 22 $Kg/cm^2$ were filled, and even if the temperature was elevated to 170° to 180° C. by heating, gas absorption did not occur at all. Thus, it was confirmed that when a common cobalt compound other than the $\beta$-dioxo cobalt compound is used, a catalyst having a capacity of causing the oxo reaction of ethylene under mild conditions as described above cannot be prepared at all.

EXAMPLE 12

An autoclave was charged with 4 millimoles of bisacetylacetonato-cobalt, 4 millimoles of 2-pyridone and 50 ml of benzene, and carbon monoxide under a pressure of 20 $Kg/cm^2$ and hydrogen under a pressure of 20 $Kg/cm^2$ were filled in the autoclave. Heating was conducted at 170° C. for 30 minutes to form a catalyst. The autoclave was cooled and the residual gas was released. Then, 98 millimoles of ethylene was charged in the autoclave together with carbon monoxide of a pressure of 22 $Kg/cm^2$ and hydrogen of a pressure of 22 $Kg/cm^2$. The reaction was carried out at 120° C. for 15 minutes. The conversion of ethylene was 89.1%, and the selectivities to propionaldehyde and propanol were 91.4% and 4.8%, respectively, the total selectivity being 96.2%. A trace amount of ethane was formed.

Even if each of the partial pressures of carbon monoxide and hydrogen was reduced at the catalyst-forming step, the reaction was advanced at an ethylene conversion of 90.2%. The selectivity to propionaldehyde was 78%, and trace amounts of propanol and ethane were formed. The gas absorption speed was 331 moles per mole of Co per hour. The catalyst was phase-separated as in Example 8, and it could easily be recovered and used repeatedly for the reaction.

EXAMPLES 13 TO 15

A catalyst was prepared in the same manner as in Example 12 except that 4 millimoles of bisacetylacetonato-cobalt dihydrate (I), bis(methylacetoacetato)-cobalt (II) or bis(diethylmalonato)-cobalt (III) was used as the $\beta$-dioxo cobalt compound, and by using the thus-prepared catalyst, ethylene was reacted under the same conditions as in Example 12. The reaction was advanced at a gas adsorption speed of about 300 moles per mole of Co per hour. In each case, the catalyst was phase-separated after the reaction and could be used repeatedly for the reaction. The conversion of ethylene and the selectivity of the converted ethylene were as shown in Table 3.

TABLE 3

| Example No. | β-Dioxo Cobalt Compound | Partial Pressure of Each of Carbon Monoxide and Hydrogen at Catalyst-Forming Step | Reaction Conditions | Conversion (%) | Selectivity (%) | | |
|---|---|---|---|---|---|---|---|
| | | | | | propion-aldehyde | pro-panol | ethane |
| 13 | (I) | 15 Kg/cm$^2$ | 110° C., 25 minutes | 87.1 | 91.0 | trace | trace |
| 14 | (II) | 15 Kg/cm$^2$ | 110° C., 25 minutes | 87.1 | 86.1 | trace | trace |
| 15 | (III) | 15 Kg/cm$^2$ | 110° C., 25 minutes | 95.7 | 88.7 | 3.5 | trace |

EXAMPLE 16

The reaction was carried out under the same conditions as in Example 12 except that 10 millimoles of 2-ethylpyridine was used instead of 2-pyridone. The conversion of ethylene was 95.5%, and the selectivities of the converted ethylene to propionaldehyde, n-propanol and ethane were 91.2%, 2.1% and 0.7%, respectively. The gas absorption speed was 409 moles per mole of Co per hour.

EXAMPLE 17

The reaction was carried out under the same conditions as in Example 12 except that 10 millimoles of 2-propylpyridine was used instead of 2-pyridone. The conversion of ethylene was 94.8%, and the selectivities of the converted ethylene to propionaldehyde, n-propanol and ethane were 90.5%, 2.4% and 0.7%, respectively. The gas absorption speed was 379 moles per mole of Co per hour.

EXAMPLE 18

In the same manner as described in Example 12, a catalyst was prepared by using 4 millimoles of bisacetylacetonato-cobalt, 4 millimoles of 2-quinolinol (2-hydroxyquinoline) and 50 ml of tetrahydrofuran. By using the thus-prepared catalyst, the oxo reaction of ethylene was carried out at 120° C. The reaction was advanced at a gas absorption speed of 300 moles per mole of Co per hour to obtain propionaldehyde.

The separation of the catalyst from the reaction mixture and repeated use of the separated catalyst according to the present invention will now be described by reference to the following Examples.

EXAMPLE 19

An autoclave was charged with 4 millimoles of bis-(acetylacetonato)-cobalt, 4 millimoles of 2-pyridone and 50 ml of ethylbenzene, and carbon monoxide under a pressure of 20 Kg/cm$_2$ and hydrogen under a pressure of 20 Kg/cm$^2$ were filled into the autoclave. Then, the autoclave was heated at 170° C. for 30 minutes to prepare a catalyst. The autoclave was cooled and the residual gas was released. Then, 98 millimoles of ethylene and 10 ml of polyethylene glycol having an average molecular weight of 400 were charged into the autoclave together with carbon monoxide of a pressure of 22 Kg/cm$^2$ and hydrogen of a pressure of 22 Kg/cm$^2$. The reaction was conducted at 120° C. for 15 minutes. The conversion of ethylene was 90.0% and the selectivity to propionaldehyde was 75%. To the liquid reaction mixture was added 50 ml of hexane, and the mixture was allowed to stand still for 30 minutes. The liquid reaction mixture was separated into a lower layer of a red solution containing the catalyst and polyethylene glycol and an upper layer of a colorless transparent solution containing propionaldehyde, ethylbenzene and hexane. The concentration of cobalt in the upper layer was 11 ppm, which corresponded to only 0.36% of the total amount of cobalt. When the liquid reaction mixture was allowed to stand still without addition of hexane, the mixture was separated into two liquid phases completely in 4 to 5 hours.

The polyethylene glycol solution containing the catalyst was recovered and 50 ml of ethylbenzene was added thereto. The liquid was charged in the autoclave, and ethylene, carbon monoxide and hydrogen were filled in the autoclave and the second reaction was carried out in the same manner as described above. The conversion of ethylene was 89.7% and the selectivity to propionaldehyde was 82.0%. The gas absorption speed was 411 moles per mole of Co per hour and was higher than the gas absorption speed attained in the first reaction (331 moles per mole of Co per hour). The separability of the catalyst was as good as in the first reaction.

EXAMPLE 20

The first reaction was carried out under the same conditions as in Example 19 except that 50 ml of toluene was used instead of ethylbenzene. A liquid reaction mixture containing propionaldehyde was obtained with a selectivity of 79.0%. Hexane was added to the liquid reaction mixture, and the resulting liquid was allowed to stand still. A polyethylene glycol solution containing the catalyst, which was separated as the lower layer, was mixed with 40 ml of toluene, and the mixture was charged in the autoclave. Then, 98 millimoles of ethylene was filled in the autoclave together with carbon monoxide of a pressure of 22 Kg/cm$^2$ and hydrogen of a pressure of 22 Kg/cm$^2$, and the second reaction was carried out. The selectivity to propionaldehyde was increased to 90.7%, but the gas absorption speed (323 moles per mole of Co per hour) was not substantially changed from the gas absorption speed attained at the first reaction (348 moles per mole of Co per hour).

EXAMPLE 21

The reaction was carried out in the same manner as in Example 20 except that benzene was used instead of toluene, and the catalyst solution recovered by using polyethylene glycol having an average molecular weight of 400 in the same manner as in Example 20 was used repeatedly for the reaction. The selectivity to propionaldehyde was 78.5% in the first reaction, 88.2% in the second reaction and 88.0% in the third reaction. The separability of the catalyst from the liquid reaction mixture was slightly poorer than in Examples 19 and 20 using ethylbenzene or toluene. For the fourth reaction, a mixture of 10 ml of benzene and 40 ml of polyethylene glycol having an average molecular weight of 400 was added to the lower layer of the catalyst solution instead of benzene alone, and the fourth reaction of hydroformylation of ethylene was carried out in the same manner. The separability of the catalyst was improved, but the gas absorption speed was drastically lowered and was only 24 moles per mole of Co per hour (the gas absorption speed was in the range of from 220 to 308 moles per mole of Co per hour in the first to third reactions).

EXAMPLE 22

An autoclave was charged with 2 millimoles of dicobalt octacarbonyl, 4 millimoles of 2-pyridone, 50 ml of benzene and 4 millimoles of dimethylformamide, and 98 millimoles of ethylene was filled in the autoclave together with carbon monoxide of a pressure of 22 Kg/cm$^2$ and hydrogen of a pressure of 22 Kg/cm$^2$. The reaction was carried out at 120° C. for 15 minutes. When the liquid reaction mixture was allowed to stand still, a reddish brown catalyst solution was separated as a lower layer. The conversion of ethylene was 88.6%, the selectivity to propionaldehyde was 83.2% and the gas absorption speed was 407 moles per mole of Co per hour.

The embodiments of the invention in which an exclusive property or privilege is claimed are defined as follows:

1. In a catalytic hydroformylation process for preparing an aldehyde, wherein an ethylenically unsaturated compound selected from the group consisting of ethylene, propylene, 1-hexene, 2-octene, 1-decene, 2-ethyl-1-octene, cyclohexene, butadiene, styrene, allyl alcohol, allyl acetate, 1,1-diethoxy-propene-2, methyl acrylate and 2-vinyl-4-methyl-1,3-dioxane, is reacted with carbon monoxide and hydrogen, under hydroformylation conditions of a combined pressure of carbon monoxide and hydrogen of from 10 to 100 atmospheres, at a temperature of 70° to 150° C., the improvement which comprises: the hydroformylation reaction is carried out in the presence of a catalytically effective amount of a catalyst formed by reacting at from 50° to 120° C., under a carbon monoxide pressure of 5 to 30 atmospheres, in an organic solvent, a cobalt carbonyl compound selected from the group consisting of dicobalt octacarbonyl and hydrocobalt tetracarbonyl, with from 0.25 to 2.0 equivalents, based on the number of cobalt atoms of said cobalt carbonyl compound, of a nitrogen-containing heterocyclic compound which is substituted with an enolic hydroxyl group on the carbon atom adjacent to the ring-forming nitrogen atom, wherein said heterocyclic compound is selected from the group consisting of pyridine, quinoline, isoquinoline, pyrimidine, pyrazine, quinoxaline, pyrrole, tetrahydropyridine, oxazole, dihydroxazine and epsilon caprolactam to form a complex of said cobalt carbonyl compound and said heterocyclic compound which is capable of being precipitated when the hydroformylation reaction mixture is cooled.

2. A process according to claim 1 in which said nitrogen-containing heterocyclic compound having an enolic hydroxyl group on the carbon atom adjacent to the ring-forming nitrogen atom is selected from the group consisting of 2-hydroxypyridine, 2-hydroxy-5-methylpyridine, 2-hydroxy-6-chloropyridine, 2-hydroxy-5-cyanopyridine, methyl 2-hydroxyisonicotinate, 2,6-dihydroxypyridine, 2-hydroxyquinoline, 1-hydroxyisoquinoline, 2,3-dihydroxyquinoxaline, 2-hydroxy-3,4,5,6-tetrahydropyridine, ε-caprolactam and tautomeric isomers thereof.

3. A process according to claim 1 in which said nitrogen-containing heterocyclic compound is 2-hydroxypyridine.

4. A process according to claim 1 in which the hydroformylation reaction and the catalyst-forming reaction are carried out in the presence of an inert organic solvent effective to permit said reactions to progress and effective to permit separation of the catalyst from the reaction mixture after the hydroformylation reaction is completed.

5. A process according to claim 1 in which the hydroformylation reaction product is cooled and is distilled under reduced pressure to remove the reaction product as the overhead, and recovering the catalyst from the still bottoms by phase separation.

6. A process according to claim 4 which comprises adding a material selected from the group consisting of polyethylene glycol having a molecular weight of below about 600 and dimethylformamide, to the hydroformylation reaction mixture in an amount of from about 0.05 to about 1 parts by volume per 1 part by volume of the solvent, and after completion of the hydroformylation reaction allowing the reaction mixture to stand still to separate the reaction mixture into a phase of said material containing catalyst therein and a solvent phase containing the reaction product.

7. A process according to claim 1 in which said ethylenically unsaturated compound is ethylene, propylene, allyl acetate or 2-vinyl-4-methyl-1,3-dioxane.

8. In a catalytic hydroformylation process for preparing an aldehyde, wherein an ethylenically unsaturated compound selected from the group consisting of ethylene, propylene, 1-hexene, 2-octene, 1-decene, 2-ethyl-1-octene, cyclohexene, butadiene, styrene, allyl alcohol, allyl acetate, 1,1-diethoxy-propene-2, methyl acrylate and 2-vinyl-4-methyl-1,3-dioxane, is reacted with carbon monoxide and hydrogen, under hydroformylation conditions of a combined pressure of carbon monoxide and hydrogen of from 10 to 100 atmospheres, at a temperature of 70° to 150° C., the improvement which comprises: the hydroformylation reaction is carried out in the presence of a catalytically effective amount of a catalyst formed by reacting a β-dioxo cobalt compound with carbon monoxide and hydrogen under a carbon monoxide pressure of at least about 15 Kg/cm$^2$ and a hydrogen pressure of at least 15 Kg/cm$^2$ and a total pressure not in excess of 100 Kg/cm$^2$ and a temperature of at least about 150° C., in an organic solvent, in the presence of from 0.25 to 2.0 equivalents, based on the cobalt atoms of said cobalt compound, of a nitrogen-containing base selected from the group consisting of 2-pyridone, 5-methyl-2-pyridone, 6-chloro-2-pyridone, 5-cyano-2-pyridone, methyl 2-hydroxyisonicotinate, 2,6-dihydroxypyridine, 2-hydroxyquinoline, 1-hydroxyisoquinoline, 2,3-dihydroxyquinoxaline, delta valerolactam, epsilon caprolactam, 3-pyridone, 4-pyridone, 8-hydroxyquinoline, 2-pyridyl methanol, 2-(2-pyridyl)ethanol, 2-aminopyridine, picolinic acid, 3-cyanopyridine, 2-chloropyridine, 2-vinylpyridine, 2,4-lutidine, 3,4-lutidine, 2,6-lutidine, 3,5-lutidine, 2,4,6-collidine, 2-methyl-5-ethyl-pyridine, 2-propylpyridine, 2-ethylpyridine, α-picoline, β-picoline, γ-picoline and pyridine, to form a complex of cobalt carbonyl compound with said base which can be separated as an oil or a precipitate when the hydroformylation reaction mixture is cooled.

9. A process according to claim 8 in which said β-dioxo cobalt compound is cobalt compound of a β-dioxo compound selected from the group consisting of acetylacetone, 3-methyl-2,4-pentanedione, propionylacetone, benzoylacetone, benzoylacetophenone, methyl acetoacetate, ethyl acetoacetate, ethyleneglycol diacetoacetate, ethyl propionylacetate, methyl butyrylacetate, α-acetyl-γ-butyrolactone, diethyl malonate, diethyl methylmalonate and dehydroacetic acid.

10. A process according to claim 8 in which the hydroformylation reaction and the catalyst-forming reaction are carried out in the presence of an inert organic solvent effective to permit said reactions to progress and effective to permit separation of the catalyst from the reaction mixture after the hydroformylation reaction is completed.

11. A process according to claim 8 in which said β-dioxo cobalt compound is selected from the group consisting of bisacetylacetonato-cobalt, bispropionylacetonato-cobalt, bis(methylacetoacetato)-cobalt and bis(diethyl malonato)-cobalt.

12. A process according to claim 8 in which said β-dioxo cobalt compound is bisacetylacetonato-cobalt.

13. A process according to claim 8 in which said nitrogen-containing base is selected from the group consisting of 2-pyridone, 5-methyl-2-pyridone, 6-chloro-2-pyridone, 5-cyano-2-pyridone, methyl 2-hydroxyisonicotinate, 2,6-dihydroxypyridine, 2-hydroxyquinoline, 2,3-dihydroxyquinoxaline, δ-valerolactam and ε-caprolactam.

14. A process according to claim 8 in which the hydroformylation reaction product is cooled and is distilled under reduced pressure to remove the reaction product as the overhead, and recovering the catalyst from the still bottoms by phase separation.

15. A process according to claim 8 which comprises adding a material selected from the group consisting of polyethylene glycol having a molecular weight of below about 600 and dimethylformamide, to the reaction mixture in an amount of from about 0.05 to about 1 parts by volume per 1 part by volume of the solvent, and after completion of the hydroformylation reaction allowing the reaction mixture to stand still to separate the reaction mixture into a phase of said material containing catalyst therein and a solvent phase containing the reaction product.

16. A process according to claim 8 in which said ethylenically unsaturated compound is ethylene, propylene, allyl acetate or 2-vinyl-4-methyl-1,3-dioxane.

* * * * *